United States Patent [19]

Akakawa

[11] Patent Number: Plant 6,691

[45] Date of Patent: Mar. 21, 1989

[54] CLEMATIS PLANT NAMED HAKUBA

[75] Inventor: Hiroshi Akakawa, Azumi, Japan

[73] Assignee: Sakata Seed America, Inc., San Francisco, Calif.

[21] Appl. No.: 110,888

[22] Filed: Oct. 21, 1987

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A cultivar of Clematis named Hakuba, having a compact growth habit, large pale violet flowers having 6–8 petals and carried on short stems, white to pale yellow stamens displayed prominently in center of flower, and by its adaptability to outdoor growth or pot culture.

1 Drawing Sheet

The present invention relates to a new and distinct cultivar of clematis plant known by the cultivar name Hakuba.

Flower-bearing clematis plants are one of the most spectacular of all flowering vines, and relatively easy to grow and maintain. The genus Clematis is very large, having as many as perhaps 300 different species. The species of clematis which comprises the present invention is a perennial and well-known for bedding purposes.

Traditionally, Clematis have been used as bedding plants or climbers due to the vine characteristics of the species. The development of cultivars for pot plant culture has accordingly centered around vine cultivars, with less than fully satisfactory results.

With the foregoing in mind, a breeding program was established by applicant in Nagano, Japan, the specific purpose of which was to develop a perennial clematis that could be used both as a bedding plant and in pot plant programs. Applicant was particularly interested in developing a new cultivar that could exhibit consistently good and uniform pot performance.

Hakuba was originated from a hybridization made in 1973 in the controlled breeding program in Nagano, Japan referred to above. The female parent was Mrs. Spencer Castle, and the male parent was Madam Van Hote, with both cultivars being unpatented. The new cultivar Hakuba resulted from the selection and reselection by applicant of plants constituting the progeny of the stated parentage, and was selected primarily for its attractive pale violet or lavender flower color, its large flower petals, and its dwarf habit.

The first act of asexual reproduction of Hakuba was subsequently accomplished when cuttings were taken from the finally selected plant of the progeny of the stated cross by applicant in a controlled environment in Nagano, Japan. Horticultural examination of the plant resulting from asexual reproduction has demonstrated that the combination of characteristics as herein disclosed for Hakuba are firmly fixed and are retained through successive generations of asexual reproduction.

Hakuba has not been observed under all possible environmental conditions. The phenotype may vary significantly with variations in environment such as temperature, light intensity, and day length. The following observations, measurements and comparisons describe plants grown in Nagano, Japan under growing conditions which are similar to those generally used in commercial practice.

The following traits have been repeatedly observed and are determined to be basic characteristics of Hakuba, which in combination distinguish this Clematis as a new and distinct cultivar:

(1) The flower stems are very short in relation to other cultivars of this type, thereby producing a unique compact plant having what is essentially a dwarf habit. This dwarf habit is unique, to the best of applicant's knowledge.

(2) The overall flower size is very large, being 5.5 to 6.5 inches in diameter. The flower color is a pale violet or lavender, with the flowers when just opening being a brighter lavender-pink.

(3) The mature stamens at the center of the flower are white in color, and the number and radial direction of the stamens from the center of the plant provide an attractive contrast with the flower petals.

(4) The number of flower petals varies from 6 to 8, and the petals are relatively flat when the flower is fully open.

(5) The new cultivar can be grown outdoors as a bedding plant, or in pot plant programs. The normal blooming period for Hakuba when grown outdoors in May and June, and then again in September. When grown indoors in pot plant programs, flowering occurs approximately 6–7 months after the rooting of cuttings, depending upon growth conditions and controls. When grown as a pot plant, the plant height is a very compact 10–15 inches which, together with the large flower size, creates a striking appearance.

(6) Hakuba has short internodes, with the node at previous shoots evolving into a flower bud.

It is difficult to compare Hakuba with known clematis cultivars. The novel characteristics noted above, particularly its dwarf habit, very short stems and large flowers, make Hakuba a truly unique new cultivar.

The accompanying color photographic drawings show typical inflorescence and foliage characteristics of Hakuba, with colors being as nearly true as possible with illustrations of this type. The photograph at the top of the drawing sheet is a top perspective view of the new cultivar, with the unique characteristics of the cultivar being clearly apparent. The color photograph at the bottom of the sheet is a closeup of several flowers, showing in more detail the shape and number of the flower petals, and the stamens emanating radially from the center of the flower.

In the following description, color references are made to The Royal Horticultural Society Colour Chart, except where color designations of ordinary dictionary significance are used. The color values were determined at Nagano, Japan.

Classification:

*Botanical.*—Clematis cv. Hakuba.

*Commercial.*—Clematis.

Parentage:

*Male parent.*—Madam Van Hote.

*Female parent.*—Mrs. Spencer Castle.

Plant:

*Form and size.*—Symmetrical in form and essentially dwarf. The flower stems are very short, producing a dwarf plant having a canopy of large flowers immediately above the foliage.

*Growth habit.*—Very compact.

*Foliage.*—Size: Average. Quantity: Abundant. Color: Dark green, upper surface approximately 139A; veins light green and visible on upper surface. Shape: Generally heart-shaped. Texture: Dull.

Flowers:

*Form.*—Generally round, with 6–8 petals of equal size.

*Size.*—Overall diameter 5.5 to 6.5 inches, very large.

*Borne.*—On very short stems, just above the foliage.

*Quantity.*—Floriferous.

*Blooming period.*—In outdoor plantings in Nagano, Japan blooming periods are May–June and again in September; in greenhouse pot culture, flowering is approximately 6–7 months from rootings of cuttings. Greenhouse flowering is normally March or April.

*Color.*—Fully open, upper surface — 84D. Half open (not shown), upper surface — brighter and darker than 84D.

*Reproductive organs.*—Stamens (yellowish to white) extend radially outwardly from the center and form an attractive flower center; reproductive organs otherwise normal.

I claim:

1. A new and distinct cultivar of Clematis named Hakuba, as illustrated and described.

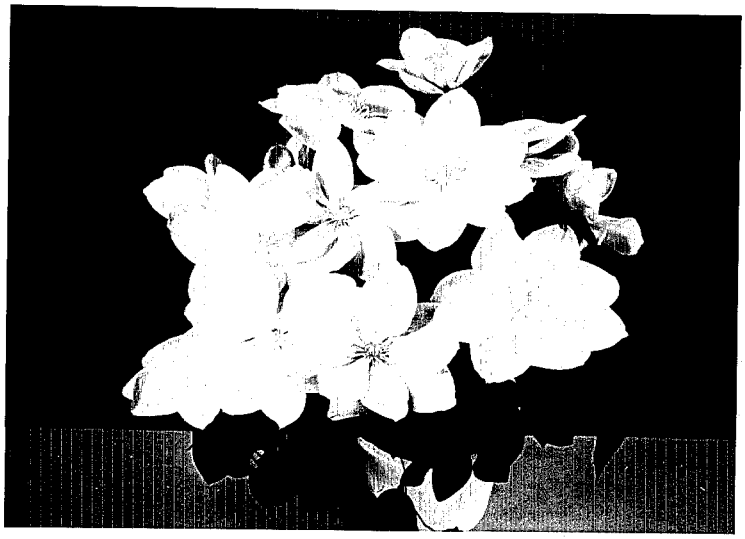
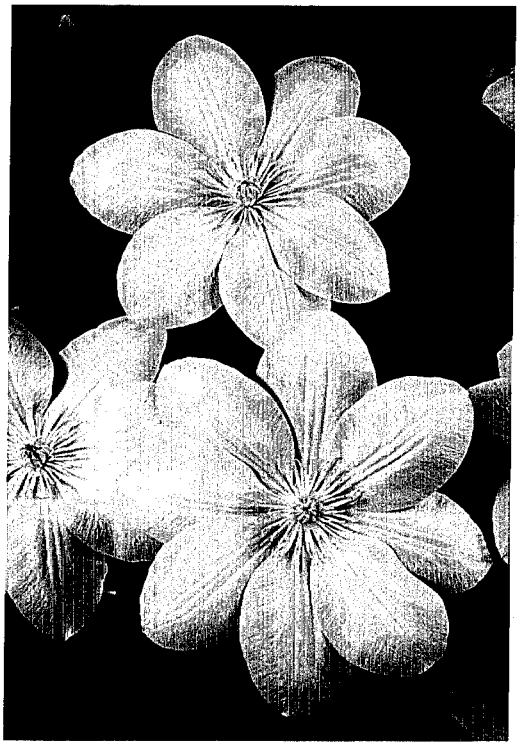

* * * * *